United States Patent [19]

Bowers

[11] 4,399,821

[45] Aug. 23, 1983

[54] FREE MOVING ANIMAL PHYSIOLOGICAL MONITORING AND IDENTIFICATION SYSTEM AND METHOD

[76] Inventor: David L. Bowers, 17399 Plaza Dolores, San Diego, Calif. 92128

[21] Appl. No.: 236,058

[22] Filed: Feb. 19, 1981

[51] Int. Cl.³ .............................................. A61B 5/00
[52] U.S. Cl. .................................. 128/630; 340/573; 128/421
[58] Field of Search ............... 128/631, 653, 903, 904, 128/905; 340/573, 575

[56] References Cited

U.S. PATENT DOCUMENTS

| | | | |
|---|---|---|---|
| 3,364,929 | 1/1968 | Ide et al. | 128/419 R |
| 3,478,344 | 11/1969 | Schwitzgebel et al. | 128/903 |
| 3,972,320 | 8/1976 | Kalman | 128/903 |
| 4,226,229 | 10/1980 | Eckhart | 128/66 |
| 4,232,682 | 11/1980 | Veth | 128/689 |
| 4,262,632 | 4/1981 | Hanton | 128/631 |
| 4,305,402 | 12/1981 | Katims | 128/421 |

OTHER PUBLICATIONS

Los Alamos Scientific Laboratory (LASL) Related Document: "Present Status of Electronic Identification," LASL Ref. No. LA-UR-80-3166, Nov. 3-7, 1980, Dale M. Holm et al.
Los Alamos Scientific Laboratory (LASL) Related Document: "Electronic Identification", Oct. 1, 1978-Sep. 30, 1979, LASL Ref. No. LA-8315-PR, Aug. 1980.
Livestock Conservation Institute, National Livestock Electronic Identification Board, Meeting Minutes and Related Documents: Nov. 3, 1980, held at Galt House, Louisville, KY.
Long, Francis M. and Weeks, Richard W., "Wildlife Biotelemetry: Frustrating But Fun, Part I," IEEE-/EMBS Newsletter, vol. 19, No. 2, 9-10, Jun. 1980.
Long, Francis M. and Weeks, Richard W., "Wildlife Biotelemetry: Part II," IEEE/EMBS Newsletter, vol. 19, No. 3, 6-8, Sep. 1980.
Long, Francis M. and Weeks, Richard W., "Don't Badger Me!! Wildlife Biotelemetry, Part III (conclusion)," IEEE/EMBS Newsletter, vol. 19, No. 4, 19-23, Dec. 1980.
Animark, Inc., Brochure Describing the Pregnosticator TM Line of Electronic Animal Pregnancy Detectors.

*Primary Examiner*—William E. Kamm
*Attorney, Agent, or Firm*—Woodcock, Washburn, Kurtz, Mackiewicz & Norris

[57] ABSTRACT

An animal physiological monitoring and identification system and method for carrying out same, wherein each animal within the system is provided with an implanted device equipped with means for deriving the data representative of one or more animal physiological parameters, such a device also holding stored animal identification data and being equipped to communicate data to and from external data handling and interrogation devices. Each implanted device provides for delivery of stimulation pulses or signals to a portion of the animal, such as a selected muscle area, for evoking an animal response such as twitching which is readily observable externally.

26 Claims, 1 Drawing Figure

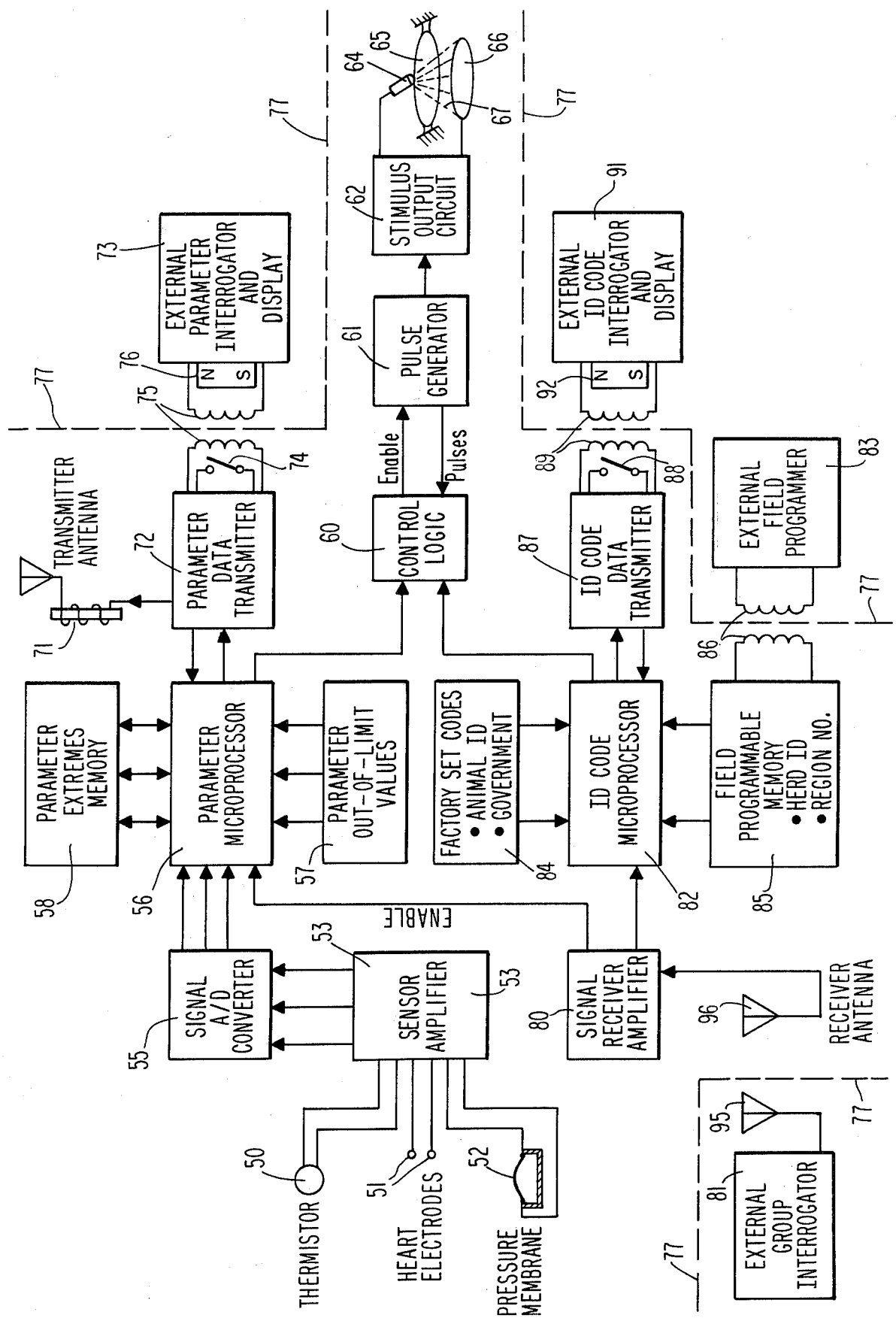

FREE MOVING ANIMAL PHYSIOLOGICAL MONITORING AND IDENTIFICATION SYSTEM AND METHOD

BACKGROUND OF THE INVENTION

This invention relates to animal physiological monitoring and identification devices and, more particularly, to a system and method for monitoring one or more physiological parameters of each of a plurality of animals and for providing means of observing those animals which have parameters which are outside of predetermined limits. The system of this invention also comprises means to identify said monitored animals.

Prior devices and systems for monitoring animal data have been concentrated primarily in the area of wildlife biosystems, primarily utilized to obtain movement and animal ID data. In these systems radio tags are used as the means of obtaining source data for animal movement studies. Such wildlife tag uses have produced significant improvements in implantable transmitters, receivers for picking up low level signals from the animal transmitters, and associated telemetry improvements. The state of the art in this area is now well developed, and it is known that implanted devices can be confidently utilizied in free moving animals. There has been a lesser amount of activity in the area of farm animals, i.e., herds which are confined generally in terms of the area of movement of the individual animals. There is some limited patent literature in this area, showing the use of attached or implanted devices. However, there has been a lack of, and there remains a substantial need for, a commercially acceptable system for accurate monitoring and identifying on a group or herd basis. Further, there has been no acceptable means enabling the system manager, e.g. farmer, to go out into the field and identify individual animals on the basis of sensed physiological parameters and their associated identification codes.

SUMMARY OF THE INVENTION

It is an object of this invention to provide a system and method for accurate monitoring of animal parameter data.

It is another object of this invention to provide such an animal parameter monitoring system which provides a convenient method and means for a system operator to identify individual animals on the basis of monitored parameter data and/or animal identification data.

It is another object of this invention to provide a system for animal monitoring which provides flexible monitoring on both a group (herd) and individual basis.

It is another object of this invention to provide an animal monitoring system having means for causing an observable animal response in a selected animal and for transmitting information concerning such animal.

It is another object of this invention to provide an animal identification system which enables accurate and simple identification of animals individually or by group, on the basis of predetermined criteria.

It is another object of this invention to provide an animal monitoring system for monitoring one or more physiological parameters of each animal in a group, and for providing an animal response indication when such monitored data is out of limits.

It is yet another object of this invention to provide an improved means and method for interrogating animals having implanted monitoring devices, to enable efficient and simple animal management on the basis of monitored animal physiological data.

In accordance with the above objects, there is provided an animal physiological monitoring system, and method of monitoring, wherein each animal within the system is provided with an implanted device equipped with means for deriving the data representative of one or more animal physiological parameters, such a device also holding stored animal identification data and being equipped to communicate data to and from external data handling and interrogation devices. Each implanted device provides for delivery of stimulation pulses or signals to a portion of the animal, such as a selected muscle area, for evoking an animal response such as twitching which is readily observable externally. The logic circuitry of each implantable device enables the animal stimulation upon one or more of a variety or programmed conditions, such conditions including interrogation from an external source by the operator; detection of an out of limits condition for any one of the monitored parameters; or interrogation following storage of monitored parameter data. In addition, each animal implanted device stores animal identification data, and contains means providing for animal stimulation as a function as received identification signals compared with stored data, so as to provide an observable animal response for any animal properly addressed with given animal identification data.

BRIEF DESCRIPTION OF THE DRAWING

The drawing is a block diagram which illustrates the system of this invention. In addition, the drawing constitutes a flow diagram which illustrates the method steps of operating the system.

DESCRIPTION OF THE PREFERRED EMBODIMENT

In the description that follows, circuit blocks are described in functional terms, it being understood that corresponding circuitry is readily available and within the state of the art. Reference is made particularly to the implantable pacemaker patent art, which illustrates a wide variety of electronic circuits adaptable for signal sensing, amplifying, logic processing, programming and pulse generation. It is state of the art to fabricate such circuitry in either analog or digital form, the digital form being presently preferred because of the greater signal processing capability. The state of the art in digital processing is represented by a microcomputer system comprising a microprocessor interfacing with various memory elements. By programming the memory elements in a predictable fashion, commonly referred to as software programming, the input signal or data to the microprocessor can be controlled (processed) in a predictable manner to provide the desired output and response. As with the pacemaker art, the circuitry of this invention may be embodied on one or more solid state chips, suitably assembled together with a limited number of ICs and discrete components, as well as miscellaneous elements such as coupling coils, reed switches and other rather suitable transmit/receive components. Also, state of the art power supply elements, such as lithium batteries, are employed. While the device which is described herein is referred to as an implanted device, it is to be understood such that term is not limiting in terms of where the device may be positioned in or on the animal, and embraces devices insertable in the ear, swallowed, and located in the stomach, intestinal tract, etc.

Referring now to the Figure (which is a block diagram of the system), starting at the left hand side there are illustrated three types of sensors, which are examplary of the type of sensors utilized in this system for detection of animal physiological parameters. A thermistor 50 is illustrated which may be imbedded at an appropriate place in the animal for detection of body temperature, and generates a temperature signal which is transmitted to sensor amplifier block 53 for amplification. Likewise a pair of heart electrodes is illustrated at 51, similar to electrodes utilized in implantable cardiac pacing systems, for detection of heart signals. The heart signals are shown connected to sensor amplifier block 53, at which point additional signals may be derived representative of specific heart parameters such as heartbeat rate, Q-T interval, R-wave amplitude, etc., in a state of the art fashion. A pressure membrane 52 is illustrated, for generating an electrical signal representative of pressure at a predetermined location in the animal, which signal likewise is transmitted to sensor amplifier block 53. In addition, although not shown, other available sensors may be utilized for sensing blood chemistry parameters such as pH, PCO2, PO2, etc. Thus, while three sensor elements are shown going to the sensor amplifier block 53, there is no limitation on the number of parameters that may be monitored.

The parameters signals are inputted to a signal analog to digital A/D converter block 55, where the analog signals from the sensor amplifier 53 are converted into digital form. They are inputted into parameter microprocessor block 56, where the digital parameter signals are processed and compared with the data stored in memory. Block 57, titled Out-of-Limits (O/L) memory, read only memory (ROM) type, provides parameter limit data corresponding to each physiological parameter being monitored. For example, the body temperature limits for the animal may be stored in accordance with a lower limit of 101° F. and an upper limit of 105° F., normal temperature being 103° F., meaning that any sensed temperature equal to one of the limits or outside of this range would be O/L. Likewise, the heart rate limits may be stored as 60 bpm and 120 bpm. In block 56, the parameter microprocessor input data is compared (suitably on a periodic basis, for a digital embodiment) with the O/L data in memory 57, and a parameter output signal is developed in accordance with a detected O/L condition. The parameter output signal is connected to a control logic block 60, for processing in a manner as described further hereinbelow.

Another processing operation which is performed in the microprocessor, block 56, is that of determining extreme values of the monitored parameter, whether or not O/L. For example, if the animal body temperature has risen to 106° F., being higher than any previous detected value, this is stored in parameter extremes memory 58 (suitably RAM). Likewise, a low value extreme for each parameter is stored in memory 58. Microprocessor 56 can retrieve data from memory 58 upon a suitable instruction.

A parameter output signal from block 56, indicating the existence of an O/L condition for one of the parameters, is processed through the control logic block 60 to provide a control signal which is coupled to pulse generator 61. Pulse generator 61 provides a predetermined series of stimulating pulses, which are power amplified at stimulus output circuit 62 and suitably applied to a stimulating electrode 64 connected to animal tissue 65. A second electrode, connected to the other output terminal of circuit 62 is shown at 66, and may suitably be the conductive case of the device either in contact or at a distance from the muscle 65 as is commonly done in unipolar cardiac pacing systems. The animal tissue 65 is suitably chosen to be muscle such that when stimulated, causes visibly observable animal twitching. Thus, when stimulated, the animal twitchs in such a way that the farmer, or system operator, can visibly observe the occurence of the twitching. For good visual detection muscle twitching may be invoked by stimulation in the back of most animals, just below the neck. The location and position of the electrodes 64 and 66 depend on the type of muscle to be stimulated. For example, the neck and back muscle Longissimus Dorsi in a cow can be stimulated using a direct contact electrode 64 attached to the muscle in similar fashion as an epicardial pacemaker electrode is attached to heart muscle. The criteria for electrode placement and design is to direct stimulating current 67 through the muscle 65 to be stimulated. The important factor for effective stimulation is to have the level of current density in the muscle to be above the level of stimulus threshold, resulting in an evoked muscle response producing a reliable twitch.

While stimulation of the upper back muscles for causing twitching in the animal is preferred for livestock and many farm animals, the evoked animal response is not limited to muscle twitching. Other forms of muscle stimulation may be accomplished such as causing tail movement of the animal, causing it to run, and other visibly/observable movement responses. In addition, the implantable device stimulus output signal may be connected to other tissue structures to produce audible responses in certain animals.

For the twitching response, which is particularly well adapted for livestock, control logic 60 may generate control signals to cause pulse generator 61 to provide stimulation pulses in a series, such as to provide information regarding what parameter is out of limits, and even by how much. For example, if the Out-of-Limit parameter is temperature, control logic 60 may provide an enabling control signal to pulse generator 61 such that generator produces a given number of animal twitches corresponding to the animal temperature. If it is assumed that the lowest animal temperature that would be sensed would be 90° F., the number of twitches generated is made equal to that number which, when added to 90, makes up the animal's body temperature; if the animal's body temperature was 104° F., 14 twitches would be evoked following an external interrogation signal applied by the farmer. For systems where it is desired simply to inform the farmer, or system operator, as to which parameter is out of limits, a different output pulse rate from the pulse generator may be utilized for each respective parameter, e.g. 30 twitches per minute (tpm) for temperature; 60 tpm for heart rate; 90 tpm for pressure; 120 tpm for blood ph; etc.

Parameter data transmitter 72 is shown inter-connected with microprocessor block 56. Parameter data transmitter 72 has an antenna device or coupling means 71 for transmitting parameter data from the parameter microprocessor 56 to a remote receiver such as in a barn, or a translink station where data is collected and relayed. Thus, the parameter microprocessor 56 may be programmed such that whenever an O/L signal is developed it is transmitted from block 56 to block 72, where it is amplified and transmitted to a remote receiver, indicating that an animal in the group has an O/L condition. Likewise, the microprocessor can get data from memory 58 and couple it to transmitter 72. In addition, transmitter 72 is designed to cooperate with animal external parameter interrogator and display unit 73, which is a conventional hand held transmitter device for close proximity, low frequency or induction communication with the implanted device. The external/internal boundary for all interface devices is indicated in the drawing by a dashed line 77. Such hand held devices are in common use in the cardiac pacing art. As shown, the transmitter 72 has a normally open reed switch 74 which is closed when the magnet 76 connected to interrogator 73 is held in close proximity. Under these conditions the transmitter is activated, coupling inductive parameter data signals through the coupler 75 to the interrogator display unit 73 for parameter value display. By this means, the farmer can go around and interrogate individual animals, determining parameter values, O/L condition and the parameter extremes data stored in memory 58.

The lower portion of the drawing illustrates additional system components for animal identification communications. A signal receiver-amplifier 80 is adapted to receive through antenna structure 96 high frequency signals which are transmitted from an antenna 95 part of the external group interrogator transmitter 81, which sends out coded signals adapted for animal identification (ID) as well as parameter interrogation of a group of animals. The amplified signal containing ID code or codes from block 80 is processed in the ID microprocessor block 82 and compared with a set of stored animal identification codes. One set of stored ID codes may be factory set codes which are programmed at the factory during production and stored in memory block 84. Another set of stored ID codes are contained in memory block 85 which are field programmable and set by the operator using an external field programmer 83. The external field programmer 83 is used only when the operator wants to reprogram the implant ID memory 85, placing in memory a new herd ID code or replacing the region number of a former owner with the new owner's number. The new ID codes are selectively coupled from the programmer 83 through a frequency selective coupler 86 directly into the memory 85 where the transmitted data is decoded and placed in memory. To prevent accidental reprogramming of the memory 85, the field programmer 83 sends a special signal to the memory which unlocks the memory permitting it to receive the new ID codes.

When the comparison at the ID microprocessor 82 of the received data from the group interrogator signal 81 is positive, which means the implanted device has properly addressed the selected memory and compared data with the received data, an ID signal is generated from block 82 and coupled to control logic 60, thereby causing generation of a control signal which causes an evoked animal response. For purpose of distinguishing an evoked animal response which is due to a select identification signal, control logic block 60 may cause pulse generator 61 to generate double stimulus pulses causing twitching in pairs so that it can be determined that the response is due to select identification, and not to a parameter value or an O/L condition. For example, implant interrogation from the external group interrogator 81 can occur in the following sequence; (1) initial implant interrogation will indicate if there is any parameter O/L; this is accomplished by activating an enable line from receiver amplifier 80 to parameter microprocessor 56; (2) next interrogation will reveal the given parameter value and (3) indicate if the transmitted ID code is compared with any given ID code contained in implant memory 84 and 85.

It should be noted, the parameter and ID microprocessors 56 and 82 and their associated memory elements 58, 57 and 84, 85 can be combined together into a single microprocessor and memory structure, resulting in a complete microcomputer system capable of performing all ID/parameter monitoring and interrogation operations.

With the identification interrogation feature of this invention, the farmer can go into a field where a herd of animals is located, transmit a signal from the group interrogator transmitter 81, and visually observe which animals respond to code data in a certain classification. This can be very useful as a means of sorting animals by any particular criteria. For example, the identification data may contain coded bits relating to origin of the animal; feeding history; prior locations of the animal; age; etc. By this means, the farmer can, at any later date, go out to the herd and easily select those animals of the entire herd which meet certain criteria established on the basis of part history or any selected ID code or parameter. This can be a great utility in aiding the farmer, or systems operator, in managing the herd.

A block 87 is shown, titled ID code data transmitter. It receives data from the ID microprocessor block 82, for the purpose of transmitting it when interrogated by the ID code interrogator and display 91. Transmitter 87 also comprises a normally open switch 88, which can be closed by the magnet 92 of ID code interrogator 91, thereby enabling the transmitter. Coupling is illustrated as being inductive through coupler 89, in the same manner as transmitter interrogator pair 72, 73. By this means, the farmer can interrogate one animal at a time to determine the selected code data of that particular animal. If desired, transmitters 72 and 87 may be combined, and one interrogator may be utilized to perform the functions shown in blocks 73 and 91.

In summary, the following operations may be employed utilizing the system that has been described. These operations are set forth as modes I–VII:

I.
  a. Detect O/L with implanted device.
  b. Cause evoked animal response.
II.
  a. Detect O/L with implanted device.
  b. Store O/L occurrence data.
  c. Interrogate animal with
    i. Ext. group signal
    ii. unit signal
  d. Enable stimulation and cause animal response to indicate O/L or other parameter data.
III.
  a. Detect O/L with implanted device.
  b. Transmit high frequency signal (including O/L and ID data) to remote monitor.
    i. directly
    ii. via translink device, relay station
IV. Combine step III-b with
    i. mode I
    ii. mode II
V.
  a. Transmit group ID interrogate signal.
  b. Cause animal response for animals of selected group.

VI. Interrogate individual animal for ID data.

VII. Interrogate individual animal for parameter data.

What is claimed is:

1. A system for monitoring the physiological condition of an animal, comprising:
   an implant device positionable in or on said animal, said implant device having
   at least one sensor means for sensing a physiological parameter of said animal and producing a parameter output,
   logic means responsive to said sensor means for storing a reference value of said parameter, comparing said parameter output with said reference value and producing a logic signal when said parameter output exceeds said reference value;
   output means responsive to said logic signal for providing an electrical stimulus signal; and
   stimulus means for connecting said stimulus signal to said animal so as to evoke a response by said animal.

2. The system of claim 1 wherein said sensor means comprises means for sensing the temperature of said animal.

3. The system of claim 1 wherein said sensor means is responsive to said animal's heart rate.

4. The system of claim 1, wherein said sensor means senses pressure at a predetermined location of said animal.

5. The system of claim 1 wherein said evoked animal response is a visually observable response.

6. The system of claim 5 wherein said stimulating means comprises a muscle stimulation electrode whereby said evoked response is a muscle contraction of said animal.

7. The system of claim 6 wherein said output means further comprises a pulse generator responsive to said logic signal, said muscle stimulation electrode being responsive to the output of said pulse generator, whereby said muscle contracts with the frequency of pulses from said pulse generator.

8. The system of claim 7 comprising means for controlling the frequency of pulses from said pulse generator as a function of said parameter output.

9. The system of claim 7 wherein the number of pulses output by said pulse generator is controlled as a function of the magnitude of said parameter output.

10. The system of claim 1 wherein said logic means further includes a data transmitter means responsive to said logic signal, for transmitting parameter data external to said animal.

11. The system of claim 10 further comprising a first command module positionable external to said animal and being electro-magnetically coupled to said data transmitter for receiving data from said data transmitter.

12. The system of claim 10 further comprising a first command module positionable external to said animal and being inductively coupled to said data transmitter for receiving data from said data transmitter.

13. The system of claim 1 wherein said logic means further includes:
   a receiver for detecting an input ID coded signal,
   a code memory for storing an animal identification code; and
   a microprocessor responsive to said detected signal and to said code memory and connected to provide an output to said logic means so that said output means provides a second indication when said input ID code and said stored identification code are the same.

14. The system of claim 13 further comprising a second command module positionable external to said animal, said second command module including means for transmitting said ID data signal, which signal includes said identifier code.

15. A system for monitoring the physiological condition of an animal, comprising:
   implant means positionable internal to said animal, said implant means having
   sensor means responsive to at least one physiological parameter of said animal for generating animal parameter data,
   logic means responsive to said animal parameter data, said logic means including data means for storing parameter reference data and means for comparing said parameter data with said parameter reference data and producing a logic output when a predetermined comparison is determined;
   output means responsive to said logic output for stimulating said animal so as to produce an externally detectable animal response; and
   receiver means for receiving an interrogating signal, wherein said output means is responsive to said received interrogating signal and said logic output.

16. The system of claim 14 wherein said animal response is a visibly observable muscle response.

17. The system of claim 14, wherein said animal response is an audible response.

18. The system of claim 14, wherein said sensor means is responsive to the blood chemistry of said animal.

19. The system of claim 14, wherein said logic means further comprises identification storage means for storing animal identification data, and wherein said output means has means responsive to a received interrogating signal and to said stored identification data for stimulating said animal so as to produce an externally detectable animal response.

20. An implantable device adapted for use in agricultural animals and the like, comprising means for detecting animal Out-of-Limit parameter data, and means for stimulating an animal to provide a visible response based on said Out-of-Limit data.

21. A system for monitoring parameter data of a plurality of animals, said system comprising an implanted device in each animal, each said device having means for detecting and storing Out-of-Limit parameter data for said animal, and means for responding to an interrogation signal, means for generating an animal stimulation signal in response to said interrogation signal, and means for causing a visible animal muscular response to said stimulation signal, said system further having interrogating means for transmitting an interrogation signal for receipt by each said implanted device.

22. The system as described in claim 21, wherein said interrogating signal is a group signal for interrogating a predetermined number of said plurality of animals simultaneously.

23. The system as described in claim 22, wherein each of said implanted devices comprises means for storing identification data, and said receiver means comprises means for comparing said interrogation signal with said identification data and for enabling stimulation only upon a predetermined positive comparison.

24. The system as described in claim 23, wherein one or more of said implanted devices contains transmit means for transmitting parameter or ID data to a remote location, and wherein said receiver means comprises means for causing said transmitter means to transmit data upon receipt of a predetermined interrogation signal.

25. A system for monitoring a group of animals, comprising an implant device in each of said animals, each said device comprising identification data storage means for storing identification data, receiver means for receiving externally transmitted interrogating signals, and stimulation means for stimulating said animal to produce an observable animal response;

interrogation means for transmitting interrogating signals containing transmitted identification data to said animals; and each of said implant devices containing identification comparison means for comparing stored identification data with said transmitted identification data, and means for controlling said stimulation means to produce said animal response upon a predetermined comparison of said stored and transmitted interrogation data.

26. The system as described in claim 25, wherein each said implant device comprises means for acquiring and storing animal Out-of-Limits and extreme value data, and means for transmitting said Out-of-Limit condition and extreme value data to a location external to said animal in response to a received interrogating signal.

* * * * *